United States Patent [19]

Tidwell et al.

[11] Patent Number: 5,206,236

[45] Date of Patent: Apr. 27, 1993

[54] METHOD FOR THE TREATMENT OF MALARIA

[76] Inventors: Richard R. Tidwell, 101 Forest Ridge Dr.; J. Dieter Geratz, 713 Kenmore Rd.; James E. Hall, 2440 Springview Trail, all of Chapel Hill, N.C. 27514; Dennis E. Kyle, 9415 Curran Rd., Silver Spring, Md. 20901; Max Grogl, 3404 Tan Terra Cir., Brookville, Md. 20833; Kwasi A. Ohemeng, 112 Overlook Dr., Clinton, N.J. 08809

[21] Appl. No.: 755,228

[22] Filed: Sep. 5, 1991

Related U.S. Application Data

[63] Continuation of Ser. No. 334,590, Apr. 6, 1989, abandoned.

[51] Int. Cl.$^5$ .................. A61K 31/55; A61K 31/505; A61K 31/415; A61K 31/155
[52] U.S. Cl. .................. 514/218; 514/256; 514/402; 514/636
[58] Field of Search ............... 514/256, 218, 402, 636

[56] References Cited

U.S. PATENT DOCUMENTS

| | | | |
|---|---|---|---|
| 2,277,861 | 3/1942 | Ewins et al. | 260/564 |
| 4,546,113 | 10/1985 | Glazer | 514/636 |
| 4,933,347 | 6/1990 | Tidwell et al. | 514/256 |
| 4,963,589 | 10/1990 | Tidwell et al. | 514/636 |

FOREIGN PATENT DOCUMENTS 862602  3/1953  Fed. Rep. of Germany .

OTHER PUBLICATIONS

*Medicine*, vol. 27, p. 359 (1948).

Chemical Abstracts, 96: 134342u (1982), [E. Steck et al., Exp. Parasitol. 1981, 52(3), 404–13].
Chemical Abstracts, 99: 63892g (1983), [L. Schmidt, Am. J. Trop. Med. Hyg., 1983, 32(2), 231–57].
Chemical Abstracts, 102: 40705g (1985).
Chemical Abstracts, 71: 20824r (1969).
Chemical Abstracts, 83: 22394x (1975).
Chemical Abstracts, 86: 106191d (1977).
Chemical Abstracts 87: 134731u (1977).
Peters et al., Annals of Tropical Medicine and Parasitology, 1975, 69(3) 311–328.
J. N. Ashley et al., Journal of the Chemical Society, 1942, 103–116.
Chemical Abstracts 78: 72150g (1973).

*Primary Examiner*—Jerome D. Goldberg
*Attorney, Agent, or Firm*—W. Dennis Drehkoff

[57] ABSTRACT

A method for treating malaria which comprises to an afflicted host patient a therapeutically effective amount of a compound have the structure of formula I:

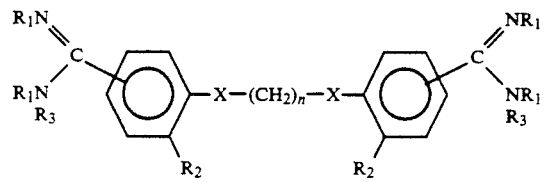

wherein X is O or NH; $R_1$ is H or two $R_1$ groups on the same amidine group together represents —$(CH_2)_m$—, wherein m=2, 3 or 4; $R_2$ is H, $NH_2$, Cl, $NO_2$; $R_3$ is H, $CH_3$ or $CH_2CH_3$ and n=2–6 or a pharmaceutically acceptable salt thereof provided that when X is O, both $R_2$ and both $R_3$ can not be H.

1 Claim, No Drawings

METHOD FOR THE TREATMENT OF MALARIA

GOVERNMENT RIGHTS

This invention was made with government support Under NO1-AI-72648 awarded by the National Institutes of Health. The government has certain rights in the invention.

This is a continuation of copending application(s) Ser. No. 334,590, filed on Apr. 6, 1989, now abandoned.

BACKGROUND OF THE INVENTION

Human malaria is caused by species of parasitic organisms of the genus Plasmodium. It is transmitted by mosquitoes which ingest sexual forms of the parasite in blood meals. Sporozoite forms of the parasite develop in the mosquito and are transmitted to new host individuals bitten by the insect. The major human pathogen is *Plasmodium falciparum*.

Malaria is one of the most important health problems in underdeveloped, tropical countries. It is estimated that more than a billion people in the world inhabit areas in which malaria is transmitted. Although chloroquine has been used as an effective drug, this drug has some side effects, but more importantly, malarial parasites have acquired a resistance to chloroquine.

Thus, malaria has become an increasing problem in the tropical zones with the advent of chloroquine resistant strains of malaria parasites coupled with a decreased effectiveness of long acting insecticides such as DDT. The magnitude of the problem is reflected in the fact that malaria is the largest infectious disease in the world. Of the one billion people residing in malaria endemia areas, approximately 25 to 200 million people are diseased at any given time.

There are estimates of a million malaria deaths a year in Africa, chiefly among children under five. Even after surviving childhood infection, a large proportion of adults nonetheless remain susceptible to infection and show periodic parasitemia, even though their serum contains "protective" antiplasmodial antibodies. In hyperendemic areas of Africa, it is believed that nearly all residents harbor a continuous series of *falciparum* infections of low to moderate pathogenicity throughout their lives.

The problem of malarial infection has become even more serious as more strains of malaria have become resistant to the major anti-malaria drug chloroquine. More and more chloroquine resistant strains of *Plasmodium falciparum* have emerged in Central and South America, Africa, and Southeast Asia.

Researchers have synthesized chemical variants of chloroquine to combat new resistant malaria strains; however, these strains have already become resistant to the new drugs. Recently a new drug, mefloquine, was introduced, but already resistant strains have appeared. A totally new drug having chemical properties different from chloroquine is needed to stem the increasing epidemic of resistant malaria strains.

Pentamidine has been known for decades and was originally shown to be useful for the treatment of trypanosomiasis. Of more recent time, pentamidine has been found to be extremely useful in the treatment of pneumocystis carinii pneumonia, especially in immunocompromised patients suffering from the acquired immunodeficiency syndrome (AIDS). However, pentamidine has not heretofore been known to have utility in the treatment of malaria.

It goes without saying that in view of the magnitude of malaria infection throughout the world, and the lack of a satisfactory agent for the treatment thereof, an urgent need exists for a more-effective anti-Plasmodia agent having good therapeutic properties.

SUMMARY OF THE INVENTION

Surprisingly, it now has been discovered that malaria may be treated with pentamidine and analogues thereof. Accordingly, the present invention provides a method for treating malaria which comprising admisistering to an afflicted host a therapeutically effective amount of compound having the structure of formula I

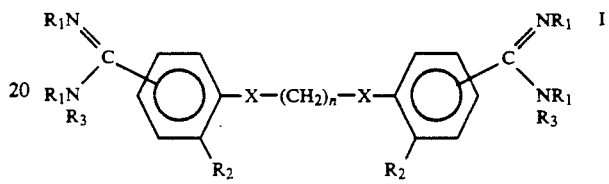

wherein X is O, N or S; $R_1$ is H or two $R_1$ groups on the same amidine group together represent $-(CH_2)_m-$, wherein $m=2$, 3 or 4; $R_2$ is H, $NH_2$, $OCH_3$, Cl, or $NO_2$; $R_3$ is H, $CH_3$ or $CH_2CH_3$ and $n=2-6$, or pharmaceutically acceptable salts thereof, or more preferably a compound of formula II:

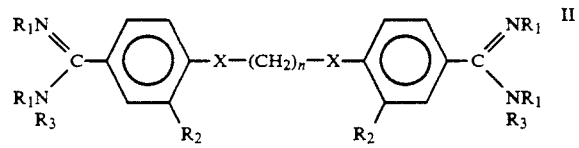

wherein X, $R_1$, $R_2$, $R_3$, m and n have the foregoing meanings, or a pharmaceutically acceptable salt thereof.

DESCRIPTION OF THE PREFERRED EMBODIMENTS DETAILED

The present invention provides a new method for treating malaria by administering compounds of formula I, above, or pharmaceutically acceptable salts thereof. Formula I encompasses pentamidine, along with various analogues or derivatives thereof, all of which are aromatic diamidines.

Obviously, the therapeutically effective dosage of any specific compound will vary somewhat from compound to compound and patient to patient. As a general proposition, a dosage from about 0.1 to about 20 mg/kg will have therapeutic efficacy. However, toxicity concerns at the higher level may restrict the dosage to a lower level such as up to about 10 mg/kg, based upon the weight of free-base. Typically, a dosage from about 0.5 mg/kg to about 5 mg/kg will be employed. The duration for the treatment is usually once per day for a sufficient length of time for the patient to become asymptomatic. Depending upon the severity of the infection in the individual patient, this may last several weeks, or longer.

In accordance with the present method, a compound of Formula I (or preferably of Formula II), or a pharmaceutically acceptable salt thereof, may be administered orally as a solid, or may be administered orally, intramuscularly, or intravenously, as a solution, suspension, or emulsion. Alternatively, the compound or salt may also be administered intravenously or intramuscularly as a liposomal suspension. Further, the compound, if hydrophobic, may be administered in an encapsulating hydrophilic liquid which can essentially encapsulate the hydrophobic compound.

Most often, the pharmaceutical compositions useful in the present invention will comprise a compound of Formula I (or preferably of Formula II), or a pharmaceutically acceptable salt thereof, in any pharmaceutically acceptable carrier. If a solution is desired, water is the carrier of choice with respect to water-soluble compounds or salts. With respect to water-insoluble compounds or salts, an organic vehicle, such as glycerol, propyleneglycol, polyethyleneglycol, or mixtures thereof, may be suitable. In the latter instance, the organic vehicle may contain a substantial amount of water. The solution in any instance should be sterilized in a suitable manner, preferably by filtration through a 0.22 micron filter. The compositions useful in the practice of the present invention may be provided in the form of vials, ampoules, and the like.

In addition to compounds of Formula I (or II), or their salts, the pharmaceutical compositions may contain other additives, such pH adjusting additives, in particular agents such as acids, bases, or buffers, including sodium lactate, sodium acetate, and sodium gluconate. Further, such compositions may contain microbial preservatives, such as methylparaben, propylparaben, and benzyl alcohol. If a multiple use vial is supplied, the pharmaceutical composition should likewise include such a microbial preservative. The formulations may be, of course, lyophilized, using techniques well known in the art.

When the desired pharmaceutical composition employs a compound of Formula I (or preferably of Formula II), or a salt thereof, which is water-insoluble, the composition may be supplied in the form of an aqueous based emulsion, containing a sufficient amount of a pharmaceutically acceptable emulsifying agent to emulsify the active compound or salt. Particularly useful emulsifying agents are phosphatidyl cholines and lecithin.

Liposomal formulations may likewise be employed in which the compound of Formula I (or preferably of Formula II), or a salt thereof, is either water-soluble, and hence entrapped within the hydrophilic center or pore of the liposome, or is water-insoluble and then substantially entrained within the hydrophobic lipid bilayer which forms the structure of the liposomes. Such liposomal formulations may be reduced in size, as through sonication and homogenization, or may be lyophilized, all using techniques well known to those skilled in the art. Alternative, if the compound or salt is hydrophobic, certain hydrophilic liquids which essentially encapsulate the hydrophobic agent at a molecular level may be employed.

In terms of the present invention, "water-soluble" is meant to define any composition which is soluble in water in an amount of about 50 mg/ml, or greater and the term "water-insoluble" is meant to define any composition which has solubility in water of less than about 20 mg/ml.

The compounds employed in the present invention in general may be synthesized in manners known and readily understood by those skilled in the art. Therefore, there is no need to explain in great detail the methodology used for the synthesis of most such compounds. Further information regarding appropriate synthesis techniques may be taken from copending application Ser. No. 262,535, Filed Oct. 25, 1988, now U.S. Pat. No. 4,933,347.

It has been found that with respect to the practice of the method of the present invention, treating malaria with a compound of Formula I (or preferably Formula II), or a pharmaceutically acceptable salt thereof, certain compounds appear to possess superior efficacy to others. Pentamidine, for example, has been found to be moderately effective against malaria, as have most of the compounds within Formula I (or II) above. It was especially surprising to find that the most efficacious product identified to date, within the scope of the present invention, is a compound No. 8 having a structure as defined by Formula II wherein $X=N$; $R_1$, $R_2$ and $R_3=H$; and $n=5$. Such a compound is identical to pentamidine, but possesses nitrogen atoms in place of the bridging oxygen atoms found in pentamidine. It was also very surprising that such a compound was the most effective compound against both the chloroquine-resistant strain (W2) and the mefloquine-resistant strain (D6).

Very close in therapeutic efficacy against malaria are compound Nos. 12, 15 and 18.

The present invention will be further described in accordance with the following non-limiting examples.

EXAMPLES 1-18

Compounds falling within the scope of Formula I (and II) were obtained, having the structures identified in Tables I through III. To test those compounds for efficacy in treating malaria the following in vitro general procedure was employed.

Chemotherapeutic Agents

Pentamidine and the analogs of pentamidine used in this study were synthesized using the procedures detailed in copending application Ser. No. 265,535, Filed Oct. 25, 1988, now U.S. Pat. No. 4,933,347.

Drug Sensitivity Assay

*Plasmodium falciparum* strains W2 (chloroquine-resistant, mefloquine-sensitive) and D6 (mefloquine-resistant, chloroquine-sensitive) were cultured in a medium consisting of RPMI-1640, 25 mM HEPES, 25 mM NaHCO$_3$, and 10% (v/v) fresh frozen human plasma. Into the wells of a 96 well microtiter plate there was placed 200 ul per well of a 1.5% erythrocyte suspension containing 0.2% to 0.4% parasitized erythrocytes containing serial dilutions of the test compounds. The plate was then placed in an anaerobic chamber, flushed with nitrogen gas and incubated at 37° C. After 24 hours, 25 ul per well of G-$^3$H-hypoxanthine (1 mCi/ml) were added and the plate reincubated as above. After 42 hours, the cells were harvested with a multimash-type cell harvester onto glass microfiber paper. A scintillation counter was used to determine the incorporated of $^3$H-hypoxanthine. The activities of the compounds tested were determined by comparing the incorporation of $^3$H-hypoxanthine to drug concentration using computerized non-linear regression analysis. [Antimicrob. Agents Chemother. 16:710, 1979; Am.J.Trop.Med.-Hygiene 34:209, 1985]. The results are shown in Tables I, II and III.

TEST RESULTS

The results of employing the foregoing procedure to determine the efficacy of compounds within the scope of Formula I (or II) above in treating malaria are contained in Tables I–III, which show that the para-amidines, meta-amidines, and para-imidazolines all have anti-plasmodial activity. The best compound for treating both strains of *Plasmodium falciparum* in accordance with the practice of the present invention is compound No. 8, defined by Formula I wherein X=N, $R_1$, $R_2$ and $R_3$=H, and n=5.

From Table II it is seen that the meta amidines are comparable to the para-amidines, although on the average they are somewhat lesser in activity than the para-amidines.

From Table III it can be seen that the compounds of Formula II wherein the amidine groups have been converted to imidazolines are as a whole essentially as efficacious as their simple amidine counter-parts.

TABLE I

*PLASMODIUM FALCIPARUM* vs. PARA-AMIDINES

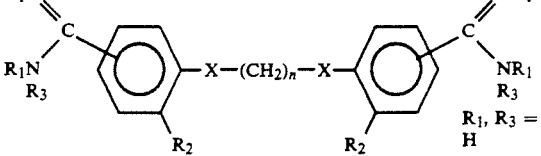

$R_1, R_3 =$ H

| EXAMPLE NO. | X | n | $R_2$ | W2 $IC_{50}$ (uM) | Rank (of 18) | D6 $IC_{50}$(uM) | Rank (of 18) |
|---|---|---|---|---|---|---|---|
| 1 | O | 3 | OCH$_3$ | 0.065 | 6 | 0.077 | 11 |
| 2 | N | 4 | H | 0.057 | 3 | 0.025 | 3/4 |
| 3 | O | 4 | H | 0.120 | 13 | 0.057 | 8 |
| 4 | O | 5 | H | 0.083 | 11 | 0.038 | 5 |
| 5 | O | 5 | NO$_2$ | 0.069 | 8 | 0.071 | 10 |
| 6 | O | 5 | NH$_2$ | 0.076 | 9 | 0.046 | 6/7 |
| 7 | O | 5 | OCH$_3$ | 0.066 | 7 | 0.106 | 14 |
| 8 | N | 5 | H | 0.022 | 1 | <0.020 | 1 |
| 9 | O | 6 | H | 0.345 | 17 | 0.118 | 16 |
| 10 | O | 5 | Cl | 0.165 | 16 | 0.107 | 15 |

TABLE II

*PLASMODIUM FALCIPARUM* vs. META-AMIDINES

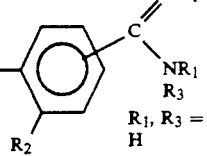

$R_1, R_3 =$ H

| EXAMPLE NO. | X | n | $R_2$ | W2 $IC_{50}$(uM) | Rank (of 18) | D6 $IC_{50}$(uM) | Rank (of 18) |
|---|---|---|---|---|---|---|---|
| 11 | O | 3 | H | 0.156 | 15 | 0.194 | 18 |
| 12 | O | 4 | H | 0.043 | 2 | 0.046 | 6/7 |
| 13 | O | 5 | H | 0.080 | 10 | 0.069 | 9 |
| 14 | O | 6 | H | 0.125 | 14 | 0.132 | 17 |

TABLE III

*PLASMODIUM FALCIPARUM* vs. PARA-IMIDAZOLINES

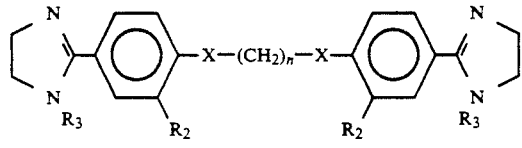

| EXAMPLE NO. | X | n | $R_3$ | $R_2$ | W2 $IC_{50}$ (uM) | Rank (of 18) | D6 $IC_{50}$ (uM) | Rank (of 18) |
|---|---|---|---|---|---|---|---|---|
| 15 | O | 5 | H | H | 0.104 | 12 | 0.023 | 2 |
| 16 | O | 5 | CH$_3$ | H | 1.817 | 18 | 0.089 | 12 |
| 17 | O | 3 | H | OCH$_3$ | 0.060 | 5/4 | 0.100 | 13 |
| 18 | O | 3 | H | H | 0.060 | 5/4 | 0.025 | 3/4 |

What is claimed is:

1. A method for treating malaria which comprises the to an afflicted host patient a therapeutically effective amount of a compound have the structure of formula I:

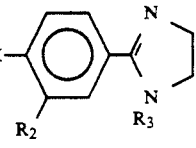

wherein X is O or NH; $R_1$ is H or two $R_1$ groups on the same amidine group together represent —(CH$_2$)$_m$—, wherein m≦2,3 or 4; $R_2$ is H, NH$_2$, OCH$_3$, Cl, NO$_2$; $R_3$ is H, CH$_3$ or CH$_2$CH$_3$ and n=2–6 or a pharmaceutically acceptable salt thereof provided that when X is O, both $R_2$ and both $R_3$ can not be H.

* * * * *